United States Patent
Lestrade et al.

(10) Patent No.: US 10,780,331 B2
(45) Date of Patent: Sep. 22, 2020

(54) DEVICE FOR BOARD SPORTS AND ASSOCIATED LEARNING METHOD

(71) Applicants: Université de Bordeaux, Bordeaux (FR); Institut Polytechnique de Bordeaux, Talence (FR); Centre National de la Recherche Scientifique, Paris (FR); École Nationale Superieure d'Arts et Metiers (ENSAM), Paris (FR); AMVALOR, Paris (FR)

(72) Inventors: Kévin Lestrade, Tarbes (FR); Jean-Luc Barou, Villenave-d'Ornon (FR); Philippe Viot, Gradignan (FR); Sandra Guérard, Leognan (FR); Patrick Lanusse, Gradignan (FR)

(73) Assignees: UNIVERSITÉ DE BOURDEAUX, Bordeaux (FR); INSTITUT POLYTECHNIQUE DE BORDEAUX, Talence (FR); CENTRE NATIONAL DE LA RECHERCHE SCIENTIFIQUE, Paris (FR); ÉCOLE NATIONAL SUPÉRIEURE D'ARTS ET MÉTIERS (ENSAM), Paris (FR); AMVALOR, Paris (FR)

( * ) Notice: Subject to any disclaimer, the term of this patent is extended or adjusted under 35 U.S.C. 154(b) by 163 days.

(21) Appl. No.: 15/740,779

(22) PCT Filed: Jun. 29, 2016

(86) PCT No.: PCT/FR2016/051623
§ 371 (c)(1),
(2) Date: Dec. 28, 2017

(87) PCT Pub. No.: WO2017/001780
PCT Pub. Date: Jan. 5, 2017

(65) Prior Publication Data
US 2018/0193712 A1       Jul. 12, 2018

(30) Foreign Application Priority Data

| Jun. 29, 2015 | (FR) | 15 56047 |
| Jul. 31, 2015 | (FR) | 15 57359 |
| May 27, 2016 | (FR) | 16 54787 |

(51) Int. Cl.
*A63F 9/24*        (2006.01)
*A63B 69/00*     (2006.01)
(Continued)

(52) U.S. Cl.
CPC ........ *A63B 69/0093* (2013.01); *A61B 5/6895* (2013.01); *A63B 24/0062* (2013.01);
(Continued)

(58) Field of Classification Search
CPC . A63B 71/06; A63B 24/0062; A63B 69/0093; A61B 5/6895
See application file for complete search history.

(56) References Cited

U.S. PATENT DOCUMENTS 5,826,578 A * 10/1998 Curchod ............. A61B 5/1121
                                                                        600/595
5,860,861 A *  1/1999 Lipps ..................... A63F 13/06
                                                                         463/36
(Continued)

FOREIGN PATENT DOCUMENTS

| DE | 202014008815 U1 | 1/2015 | |
| JP | H026075 U | 1/1990 | |
| WO | WO-0033924 A2 * | 6/2000 | ............. A63C 19/10 |

OTHER PUBLICATIONS

De Bona, D. D., et al., "Instrumentation of a Surfboard to Evaluate Surfing Performance," 2014 11th International Conference on Remote Engineering and Virtual Instrumentation (REV), IEEE, Feb. 26, 2014, pp. 339-343.
(Continued)

*Primary Examiner* — Steve Rowland
(74) *Attorney, Agent, or Firm* — Kenealy Vaidya LLP

(57) ABSTRACT

Some embodiments are directed to an analysis device for board sports, intended to be secured to a board, such as a surfboard or ski, at the interface with the user. The device includes: a force sensor designed to capture one or more forces generated by the user on the board; a position and motion sensor designed to capture the position, speed and acceleration of the board in space; and a processing unit or processor connected to the force sensor and to the position and motion sensor and designed to synchronize and process the data from the sensors.

17 Claims, 3 Drawing Sheets

(51) Int. Cl.
| | | |
|---|---|---|
| A63F 13/807 | (2014.01) | |
| A61B 5/00 | (2006.01) | |
| B63B 32/00 | (2020.01) | |
| B63B 32/70 | (2020.01) | |
| A63B 24/00 | (2006.01) | |
| A63B 71/06 | (2006.01) | |
| A63C 5/06 | (2006.01) | |
| A63C 11/00 | (2006.01) | |
| A61B 5/11 | (2006.01) | |

(52) U.S. Cl.
CPC ............... *A63B 71/06* (2013.01); *A63C 5/06* (2013.01); *A63C 11/00* (2013.01); *A63F 13/807* (2014.09); *B63B 32/00* (2020.02); *B63B 32/70* (2020.02); *A61B 5/0077* (2013.01); *A61B 5/11* (2013.01); *A63B 2024/0071* (2013.01); *A63C 2203/18* (2013.01); *A63C 2203/24* (2013.01)

(56) References Cited

U.S. PATENT DOCUMENTS

| | | | | |
|---|---|---|---|---|
| 6,699,127 | B1* | 3/2004 | Lobb | A63F 13/10 |
| | | | | 463/43 |
| 9,101,831 | B2* | 8/2015 | Sauerbrei | A63F 13/10 |
| 2002/0016204 | A1* | 2/2002 | Kanno | A63F 13/10 |
| | | | | 463/36 |
| 2003/0190951 | A1* | 10/2003 | Matsumoto | A63F 13/10 |
| | | | | 463/30 |
| 2007/0155495 | A1* | 7/2007 | Goo | A63B 24/0003 |
| | | | | 463/36 |
| 2007/0184940 | A1* | 8/2007 | Tomes | A63B 69/0093 |
| | | | | 482/92 |
| 2009/0105057 | A1* | 4/2009 | Carlson | A63B 69/0066 |
| | | | | 482/146 |
| 2009/0170605 | A1* | 7/2009 | Nelson | A63F 13/42 |
| | | | | 463/42 |
| 2014/0267743 | A1 | 9/2014 | Tapia et al. | |
| 2014/0278218 | A1 | 9/2014 | Chang | |
| 2016/0320476 | A1* | 11/2016 | Johnson | G06T 7/80 |

OTHER PUBLICATIONS

International Search Report for PCT/FR2016/051623 (dated Sep. 12, 2016), with English language translation of the ISR.
Written Opinion for PCT/FR2016/051623 (dated Sep. 12, 2016).
Examination Report issued in corresponding European patent application No. EP16744442.1 (dated Feb. 18, 2020).
Jun. 9, 2020 Notice of Reasons for Rejection issued in corresponding Japanese patent application No. JP2017-564744 with English translation.
Dezan De Bona, Daniel, et al., "Instrumentation of a Surfboard to Evaluate Surfing Performance," 2014 11th International Conference on Remote Engineering and Virtual Instrumentation (Rev), Polytechnic of Porto (ISEP) in Porto, Portugal from Feb. 26-28, 2014, pp. 339-343.
Cerevo, "Release of 'Snow-1', the first product of Smartphone-linked Sport Gear Brand "Xon", available by the end pf this year", [online], Jan. 5, 2015, Cerevo Inc., News, [search conducted on Apr. 14, 2020], Internet <URL: https://info-blog.cerevo.com/2015/01/05/843/>.

\* cited by examiner

DEVICE FOR BOARD SPORTS AND ASSOCIATED LEARNING METHOD

CROSS REFERENCE TO RELATED APPLICATION(S)

This application is a national phase filing under 35 C.F.R. § 371 of and claims priority to PCT Patent Application No. PCT/FR2016/051623, filed on Jun. 29, 2016, which claims the priority benefit under 35 U.S.C. § 119 of French Patent Application No. 1654787, filed on May 27, 2016, French Patent Application No. 1557359, filed on Jul. 31, 2015, and French Patent Application No. 1556047, filed on Jun. 29, 2015, the contents of each of which are hereby incorporated in their entireties by reference.

BACKGROUND

Some embodiments are directed to board sports, such as surfing, skiing and snowboarding.

In the following text, surfing will be taken as the main example of a board sport. However, the teaching of this text applies equally to the other board sports in which a mainly rigid element slides over a liquid or solid surface. That therefore includes skiing in all its variants, snowboard, etc.

Learning and perfecting a board sport such as surfing involves training under the watchful gaze of a trainer. The latter will watch the surfer move and, based on the defects that he or she observes, propose corrections to the sports person who will try to have the correct attitude through a succession of trials and errors.

This work is currently assisted by video cameras installed directly on the surfboard or on the coast, and which, by recording the movements of the surfer, will assist the trainer and the sports person subsequently viewing and analyzing the work carried out.

There are also sensors capable of providing real time information to the surfer on the surfing speed in relation to the waves.

SUMMARY

These learning and perfecting possibilities are therefore very qualitative and rely a lot on the experience of the trainer, or of the sports person. For example, in high-level sport, infinitesimal variations of bearing can have significant consequences on the quality of the trajectory even though they will be due only to a position very little different from the optimal position, a difference that is almost not or not at all detectable by the video recording.

It would therefore be desirable to offer sports persons and their trainers methods that make it possible to quantify the various elements of a movement and thus compare them, for example, to an ideal movement.

It may therefore be beneficial to provide a board sport device which makes it possible to acquire quantitative data thus mitigating or addressing at least some of the defects, drawbacks and obstacles discussed above.

To address or resolve one or more of the drawbacks mentioned previously, some embodiments are directed to an analysis device for board sport intended to be fixed onto a board support such as a surfboard or a ski at the interface with a user. The device includes:
  a force sensor suitable for capturing one or more forces generated by the user on the board support;
  a position and motion sensor suitable for capturing the position, the speed and the acceleration of the board support in space; and
  a processing unit or processor connected to the force sensor and to the position and motion sensor and suitable for synchronizing and processing the data from the sensors.

Features or particular embodiments that can be used alone or in combination include:
  the device can further include a camera connected to the processing unit or processor, the camera being positioned to capture the image of the user;
  the force sensor, the position and motion sensor and the processing unit or processor are associated with a sealed device positioned as an intermediary between the force sensor and the user;
  the position and motion sensor includes a 3-axis gyroscope, a 3-axis accelerometer and a magnetometer;
  the device includes a storage memory for the synchronized and/or processed data; and/or
  the device includes a transmitter for transmitting the synchronized and/or processed data in real time to an analysis and display computer via a wireless link; and
  the device is formed by a coating provided with at least one fixing zone intended to be fixed to the board support.

Some embodiments are directed to using the above device for learning and perfecting a board sport.

Some embodiments are directed to a method for learning a board sport using the above device, and the method includes;
  using the device by a user to practice the board sport and record data from the sensors of the device;
  processing the data and comparing the processed data with reference data; and
  processing and merging the data for a conversion and a display of user assessment and progress parameters.

One particular feature or embodiment is that the reference data define an optimal behavioral model of a user.

A particular feature or embodiment is that the data processing step further includes determining motions of the board support from measured data originating from the sensors via a predictive model.

A particular feature or embodiment is that the display of the assessment and progress parameters is produced in graphic form highlighting the difference in position of the user relative to the position of a reference user. Another embodiment is that the display of the assessment and progress parameters is produced in graphic form highlighting the differences in position between different users.

Some embodiments are directed to a computer program product that can be downloaded from a communication network and/or stored on a computer-readable medium and/or that can be executed by a processor. The program includes program code instructions for implementing the above learning method.

Some embodiments are directed to a device for simulating a board sport. The device includes:
  a board support such as a surfboard or a ski;
  a force sensor fixed onto the board support at the interface with a user, the force sensor being suitable for capturing all or most of the forces generated by the user on the board support;
  an actuator fixed onto the board support and suitable for displacing the board support according to 6 degrees of freedom; and a processing unit or processor connected to the force sensor and to the actuator and suitable for modifying the position of the board support as a function of the forces generated by the user and of parameters modeling an environment.

Some embodiments are directed to a board support, such as a surfboard and a ski equipped with an analysis device as defined above.

According to an advantageous form of this board support, the analysis device is incorporated in the board support.

BRIEF DESCRIPTION OF THE FIGURES

Some embodiments will be better understood on reading the following description, given purely as an example, and with reference to the attached figures in which.

DETAILED DESCRIPTION OF EXEMPLARY EMBODIMENTS

An analysis device for board sport is intended to be fixed onto a board support such as a surfboard or a ski. These two sports are given by way of example but the description can be applied to any sport in which a device slides over a liquid or solid medium. Thus, and as indicated previously, the embodiments described herein below will be centered on surfing.

Figure 1:
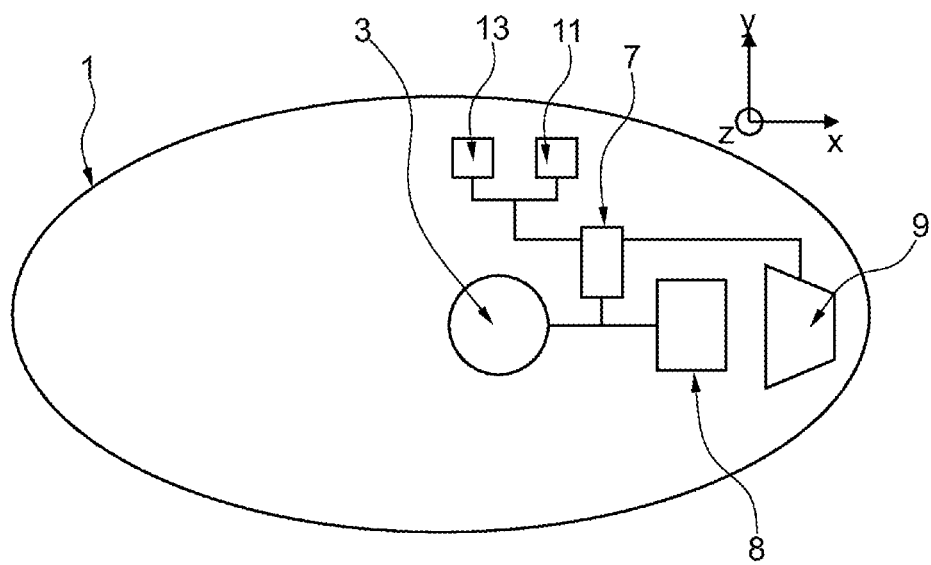
FIG. 1 represents an instrumented surfboard according to some embodiments.

Referring to FIG. 1, a surfboard 1 includes an analysis device including a force sensor 3 in the form of platform for capturing forces according to 6 components: the 3 forces according to Cartesian coordinates and the 3 movements about the axes of the Cartesian reference frame. This reference frame is defined as being linked to the surfboard, x being the longitudinal axis, y the transverse axis and z the vertical axis. It will be noted that less sophisticated sensors limited to capturing one or two force components can also be used for cost reasons. The counterpart of the use of such sensors is that the information collected is less rich. That can be compensated by preliminary studies using the platform with 6 components to determine the main components to be analyzed.

Preliminary studies make it possible to define the maximum quantities that the force sensor 3 must or should be capable of recording. Thus, it is desirable for the force sensor 3 to be capable of measuring the following maximum forces: 5000N for Fx, 5400N for Fy, 14500N for Fz, 560 Nm for Mx, 650 Nm for My and 750 Nm for Mz.

The force sensor 3 is fixed onto the surfboard 1 at the interface with a user. Thus, on a surfboard, the sensor 3 is possibly or preferably positioned under the front foot of the surfer because that is the main foot for directing the surfing. However, the sensor 3 can also be positioned under the rear foot or else two sensors are installed to collect the forces from each foot. For a ski, the force sensor is, for example, positioned under the sole of the ski boot. The force sensor thus captures all or most of the forces generated by the user on the board support. It captures both the vertical and horizontal, front and rear forces, and the rotational torques about the 3 axes, i.e. on 6 axes of freedom.

The force sensor 3 is incorporated in the surfboard 1 so as to limit as much as possible the difference in position of the user relative to a non-instrumented surfboard.

The force sensor 3 has to withstand the environmental elements of the surfboard 1 and in particular seawater whose corrosive power is well known. At the same time, any protection of the force sensor 3 must or should not disturb the measurement of the forces. For example, a sealed plastic film such as Seaguard Flex 5400, Dickson, Wasquehal, France, covering the force sensor 3 has the advantage of disturbing the capturing of the forces very little. Another solution is to use an intrinsically marine corrosion-resistant force sensor.

The analysis device also includes a position and motion sensor 5. This position and motion sensor 5 is intended to identify the interactions between the surfboard 1 and the wave by analyzing the dynamic behavior of the surfboard 1 via, for example, the angular speeds and the longitudinal accelerations of the surfboard. It is therefore suitable for capturing the position, the speed and the acceleration of the surfboard in space. It includes, for example, a three-axis gyroscope such as the ITG3200 from InvensSense, San Jose, Calif., a 3-axis accelerometer such as the ADXL345 from Analog Devices, Norwood, USA and a magnetometer, but can include or can consist of components that may be less powerful but also less costly such as a GPS receiver, or use fewer components and, for example, be limited to a GPS receiver and a 3D accelerometer of the type of those used by consumer smart phones.

A processing unit 7 is connected to the force sensor 3 and to the position and motion sensor 5. This processing unit 7 synchronizes the data from the sensors. For example, it can include or can consist of a Mega 2560 board from Arduino, Turin, Italy which also includes an analog-digital converter.

This analysis device can be distributed over several locations of the board support. For example, the position and motion sensor can be composed of several elements remotely-sited relative to the force sensor 3 and to the data processing unit 7, and so positioned by being logically connected to them, and vice versa for the other elements of the analysis device.

Advantageously, a network can be installed to recover and synchronize the information from these two sensors and also to collect and synchronize information from other sensors.

For example, a camera 9 fixed onto the surfboard 1 is connected to the processing unit 7 by this network. The camera 9 is positioned to capture the image of the user, in particular his or her foot placed on the force sensor in order to advantageously make it possible to make correlations between the forces captured and the position of the user.

The analysis device also includes a storage memory 11 for the synchronized data and/or a transmitter 13 for transmitting the synchronized and/or processed data in real time to an analysis and display computer (not represented) via a wireless link. That makes it possible to analyze the data at the end of exercise and/or while exercising.

Figure 2:
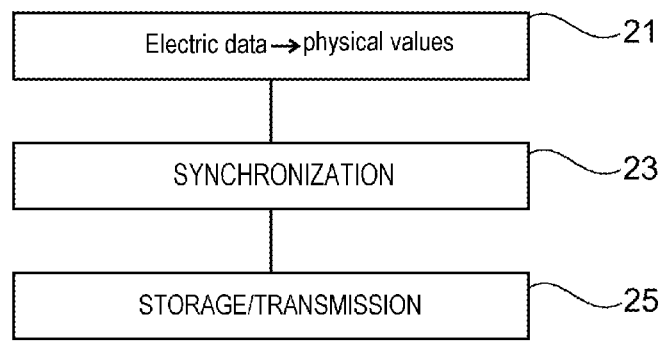
FIG. 2 represents a flow diagram of acquisition and processing of the data of the device of FIG. 1.

The processing of the data is performed as follows, FIG. 2:

Conversion, step 21, of the electrical measurements from the sensors into numeric values representing the different physical values: forces (N), moments (Nm), speeds (ms$^{-1}$) and accelerations (ms$^{-2}$) in the Cartesian reference frame x, y, z;

Synchronization, step 23, of the different measurements and, if available, of the images captured by the camera; and Storage and/or transmission, step 25, of all or most of the synchronized data.

Figure 3:
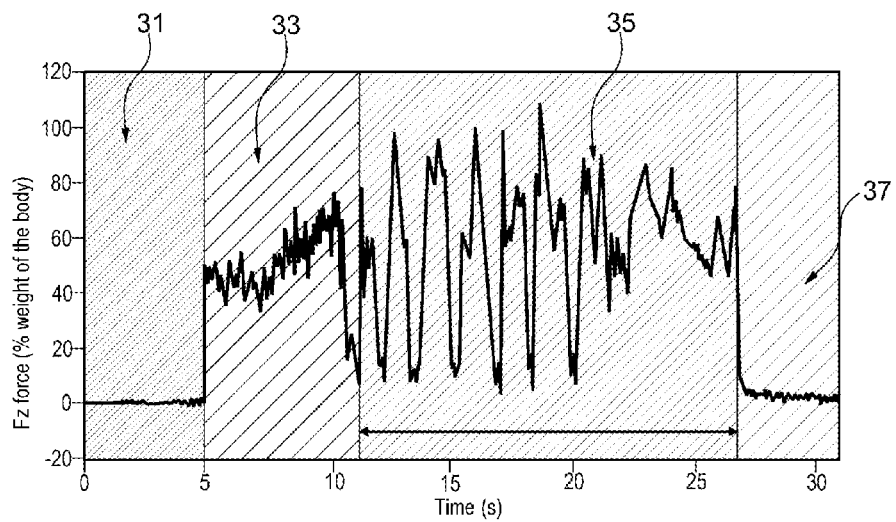
FIG. 3 represents the trend of the vertical force during a use of the device of FIG. 1.

FIG. 3 thus shows the trend of the force Fz as a function of time according to different situations.

In the zone 31, the surfer is seated on the board awaiting the wave. He or she is not therefore in contact with the force sensor 3 and the force Fz is equal to 0.

In the zone 33, the surfer is lying down on the board and rows with his or her hands to catch up with the wave. Only his or her chest is in contact with the force sensor 3 so the force Fz corresponds to approximately 40 to 60% of the weight of the surfer.

In the zone 35, the actual surfing phase starts and begins with a peak of Fz corresponding to the assumption of support of the surfer moving to the standing position. There then follows a series of presses and relaxations corresponding to the surf movements. That typically corresponds to a phase of acceleration by flexing/extension.

Finally, in the zone 37, the surfer leaves the board either by falling, or because it is the end of the wave and Fz returns to 0.

Obviously, it is the zone 35 corresponding to the surfing phase which is the most interesting to analyze.

Figures 4A, 4B:
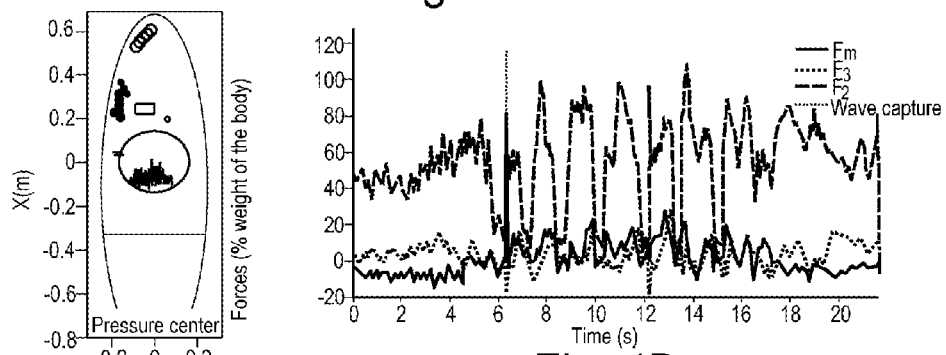
FIGS. 4A to 4D represent the trend of the forces, of the angular speeds and of the accelerations from the trend of FIG. 3.
Figures 4C, 4D:
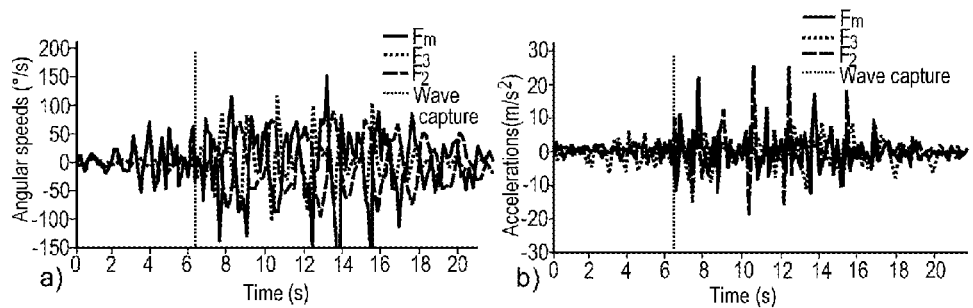

FIGS. 4B, 4C and 4D show, as a function of time and synchronized, respectively:

The vertical force;

The angular velocities; and

The longitudinal accelerations.

The dotted vertical line corresponds in these three figures to the start of the surfing phase.

Bearing in mind that the FIGS. 4 correspond to the same surfing phase as that of FIG. 3, it can be seen that the search for acceleration is reflected by acceleration peaks along the longitudinal axis: the result sought is therefore clearly achieved.

This device can advantageously be used for learning and perfecting a board sport by allowing a trainer and a sports person to see and precisely analyze what has taken place during exercise.

Figure 5:
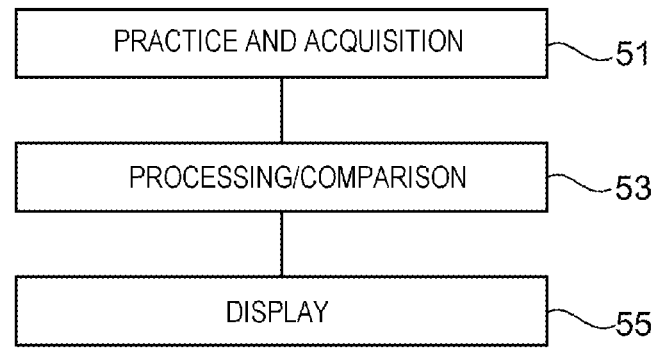
FIG. 5 represents a flow diagram of a learning method using the device of FIG. 1.

Thus, learning surfing using the surfboard includes, FIG. 5:

Use, step 51, of the surfboard by a user to practice surfing and record data from the sensors 3, 5 of the surfboard 1;

Processing of the data and comparison with reference data, step 53; and

Processing and merging of the data for conversion and display of user assessment and progress parameters, step 55.

The step 53 of data comparison can be based on data from a preceding session or data from a session of a professional surfer (thus showing "the ideal") or, finally, in a gaming activity context, the data of an "adversary".

The display of the assessment and progress parameters is produced in graphic form highlighting the difference in position of the user relative to the position of a reference user or highlighting the differences in position between different users. In a first example, several users use the same board and all or most of the changes are synthesized and placed in parallel on this display. In a second example, several users each use, in parallel, an instrumented surfboard and all or most of the changes are reported on a common display, which can allow gaming or competition applications.

For the implementation, it is conceived that the processing unit onboard the device and those used for the analysis are driven by computer programs. Thus, a computer program product that can be downloaded from a communication network and/or stored on a computer-readable medium and/or that can be executed by a processor, includes program code instructions for implementing the learning method.

Moreover, it is particularly advantageous to use the instrumented device as a basis for a simulator thus allowing a user to be trained outside of the natural environment.

Figure 6:
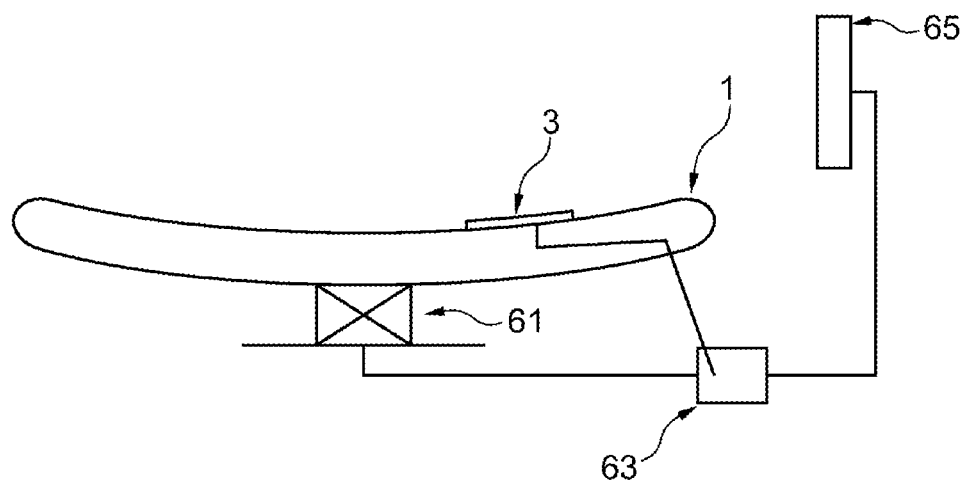
FIG. 6 represents a simulator based on the device of FIG. 1.

In particular, in FIG. 6, the simulation device includes a board support and a force sensor fixed onto the board support at the interface with a user, as described above. Furthermore, an actuator 61 is fixed onto the board support and is suitable for moving the board support according to 6 degrees of freedom. This actuator is for example a hexapod positioner or a motion platform.

It will be noted that, in this configuration, the position and motion sensor is advantageously incorporated in the actuator. It can even be eliminated by considering that the position of the surfboard is perfectly defined any instant by the positioner.

A processing unit 63 is connected to the force sensor 3 and to the actuator 61. It is suitable for modifying the position of the board support as a function of the forces generated by the user and of parameters modeling an environment in order to simulate the result of the forces applied to the board support by the user as a function of an environment programed to simulate, for example, the form of a wave, or the slope of a ski run.

For that, the modeling is based on a predictive model making it possible to predict the behavior of the board as a function of the behavior of the surfer. This model is constructed from data acquisition sessions using the surfboard 1 equipped with the analysis device described above.

This simulator also includes display screens 65 to make it possible to inform the user, in the most natural possible way, of the environment which has been programmed in order for the user to be able to react thereto.

Some embodiments have been illustrated and described in detail in the drawings and the preceding description. The latter should be considered to be illustrative and given by way of example and not as limiting some embodiments to just this single description. Many variant embodiments are possible.

For example, in the context of ski practice, it is advantageous to instrument both skis by installing, on each, a force sensor and a position and motion sensor and to synchronize all or most in order to obtain a complete set of information. In surfing, it is also possible to instrument the surfboard with a second force sensor to record the forces originating from the back foot of the surfer.

It is also possible to provide a manual on/off device allowing the user to start the acquisition only during an interesting phase of movement.

In the claims, the word "including" does not exclude other elements and the indefinite article "a/an" does not exclude a plurality.

According to some embodiments, the data processing unit 7 further includes a computation unit making it possible to analyze the data from the sensors in order to supply the user (the surfer or an external personal like the trainer) with a real time analysis of the quantitative assessment and progress information.

To this end, the data processing step 53 can include or can consist of analyzing the data from the sensors of the surfboard 1 and in comparing them to reference data. Two categories of data from the sensors are distinguished. The first category of data relates to the interactions between the surfer and the board which can be of force, pressure and/or bearing location type. The second category of data relates to the interactions between the board and the wave which can be of position, speed, acceleration type.

According to some embodiments, the computation unit includes a predictive model which makes it possible to predict the motion of the surfboard either from measured data relating to the interactions between the surfer and the board or from measured data relating to the interactions between the board and the wave.

Such quantitative information on the motion of the board is then compared to reference data which are grouped together in a database. These reference data are obtained either from a preceding session or from a session of a professional surfer. The comparison step thus makes it possible to determine the difference in position between the user relative to the position of a reference user, thus showing the points to be improved.

According to some embodiments, the image of the user, in particular his or her foot resting on the force sensor obtained from the camera 9, is synchronized with the data from the force sensors. Thus, it is possible to correlate the bearing forces with the orientation of the foot of the practicing person. This correlation allows a more precise analysis of the positioning of the foot of the practicing person to be provided.

According to some embodiments, the sealed analysis device is formed by at least one coating provided with several fixing zones to be fixed onto the board support 1. The force sensor 3, the position and motion sensor 5 and the data processing unit 7 are associated with a coating surface. When the coatings are fixed onto the board support, they form a sealed zone for the sensors 3 and 5 and the processing unit 7.

Possibly or preferably, and in the context of use of the analysis device for a surfboard, this coating takes the form of a sheet of foam with an outer surface provided with relief and an inner surface associated with the sensors 3 and 5, and with the data processing unit 7. The outer surface thus forms a non-slip surface for the board practicing person. It can take different forms and sizes according to the style of the surfing practicing person. The different coatings are arranged on the board to optimize the bearings of the practicing person. The sensors 3 and 5 and the processing unit 7 can be associated with one coating or several coatings.

Some embodiments are directed to a board support such as a surfboard or ski equipped with an analysis device which allows the person practicing a board sport to learn and improve.

The invention claimed is:

1. An analysis device for a board sport configured to be fixed onto a board support, including at least one of a surfboard and a ski, at an interface with a user, the device comprising:
    a force sensor suitable for capturing one or more forces generated by the user on the board support;
    a position and motion sensor suitable for capturing the position, the speed and the acceleration of the board support in space; and
    a processor connected to the force sensor and to the position and motion sensor and suitable for synchronizing and processing the data from the sensors, wherein the processor further includes a computation unit including a predictive model making it possible to determine the motions of the board support from measured data originating from the force sensor and the position and motion sensor.

2. The device as claimed in claim 1, further including a camera connected to the processor, the camera being positioned to capture the image of the user.

3. The device as claimed in claim 1, wherein the force sensor, the position and motion sensor and the processor are associated with a sealed device positioned as intermediary between the force sensor and the user.

4. The device as claimed in claim 1, wherein the position and motion sensor includes a 3-axis gyroscope, a 3-axis accelerometer and a magnetometer.

5. The device as claimed in claim 1, further including a storage memory for the synchronized and/or processed data.

6. The device as claimed in claim 1, further including a transmitter for transmitting the synchronized and/or processed data in real time to an analysis and display computer via a wireless link.

7. The device as claimed in claim 1, wherein the device is formed by a coating provided with at least one fixing zone intended to be fixed to the board support.

8. The use of a device as claimed in claim 1, configured for learning and perfecting a board sport.

9. A method for learning a board sport using a device as claimed in claim 1, comprising:
    using the device by a user to practice the board sport and record data from the sensors of the device;
    processing the data and comparing the processed data with reference data; and
    processing and merging the data for a conversion and a display of user assessment and progress parameters,
    wherein the data processing step further includes determining the motions of the board support from measured data originating from the sensors via a predictive model.

10. The method as claimed in one of claim 9, wherein the display of the assessment and progress parameters is produced in graphic form highlighting the difference in position of the user relative to the position of a reference user.

11. The method as claimed in claim 9, wherein the display of the assessment and progress parameters is produced in graphic form highlighting the differences in position between different users.

12. A board support, comprising: at least one of a surfboard and a ski, including the device as claimed in claim 1.

13. The board support as claimed in claim 12, wherein the device is incorporated in the board support.

14. The device as claimed in claim 2, wherein the force sensor, the position and motion sensor and the processor are associated with a sealed device positioned as intermediary between the force sensor and the user.

15. The device as claimed in claim 2, wherein the position and motion sensor includes a 3-axis gyroscope, a 3-axis accelerometer and a magnetometer.

16. The device as claimed in claim 3, wherein the position and motion sensor includes a 3-axis gyroscope, a 3-axis accelerometer and a magnetometer.

17. The device as claimed in claim 2, further including a storage memory for the synchronized and/or processed data.

* * * * *